United States Patent
Lee et al.

(10) Patent No.: US 8,673,386 B2
(45) Date of Patent: Mar. 18, 2014

(54) COMPOSITION FOR GLUCOSE SENSING COMPRISING OF NANOFIBROUS MEMBRANE AND METHOD FOR MANUFACTURING NON-ENZYMATIC GLUCOSE BIOSENSOR USING THE SAME

(75) Inventors: Kwang Pill Lee, Daegu (KR); Iyengar Gopalan Anantha, Daegu (KR); Sundaram Komathi Shanmuga, Daegu (KR)

(73) Assignee: Kyungpook National University Industry Academic Cooperation Foundation, Daegu (KR)

( * ) Notice: Subject to any disclaimer, the term of this patent is extended or adjusted under 35 U.S.C. 154(b) by 336 days.

(21) Appl. No.: 13/056,151

(22) PCT Filed: Oct. 24, 2008

(86) PCT No.: PCT/KR2008/006309
§ 371 (c)(1),
(2), (4) Date: Jan. 27, 2011

(87) PCT Pub. No.: WO2010/013865
PCT Pub. Date: Feb. 4, 2010

(65) Prior Publication Data
US 2011/0129593 A1    Jun. 2, 2011

(30) Foreign Application Priority Data
Jul. 29, 2008  (KR) .................. 10-2008-0074282

(51) Int. Cl.
*B29C 47/00* (2006.01)

(52) U.S. Cl.
USPC .......... 427/2.13; 427/2.11; 428/704; 204/415

(58) Field of Classification Search
USPC ........ 427/2, 13, 2.11, 2.13; 204/415; 428/704
See application file for complete search history.

(56) References Cited

U.S. PATENT DOCUMENTS

| | | | |
|---|---|---|---|
| 6,319,540 B1 * | 11/2001 | Van Antwerp et al. | 427/2.13 |
| 6,750,311 B1 * | 6/2004 | Van Antwerp et al. | 528/77 |
| 2010/0164488 A1 * | 7/2010 | Lowe et al. | 324/239 |

FOREIGN PATENT DOCUMENTS

| | | | |
|---|---|---|---|
| KR | 10-2000-0053776 A | | 9/2000 |
| KR | 2000-0053776 | * | 9/2000 |
| KR | 10-2005-0066059 | * | 6/2005 |
| KR | 10-2005-0066059 A | | 6/2005 |
| KR | 10-0765438 B1 | * | 10/2007 |
| WO | WO-2010/013865 A1 | * | 2/2010 |

OTHER PUBLICATIONS

Manesh et al. (Analytical Biochemistry, vol. 360, p. 1891 (2007)).*
Park et al. (J. Am. Chem. Soc., vol. 126, p. 4524 (2004)).*

* cited by examiner

*Primary Examiner* — Peter D. Mulcahy
*Assistant Examiner* — Henry Hu
(74) *Attorney, Agent, or Firm* — Rothwell, Figg, Ernst & Manbeck. P.C.

(57) ABSTRACT

Disclosed herein is a composition for glucose sensing obtained by dispersing in a solvent such as acetone a nanofibrous membrane fabricated by electrospinning a mixture containing poly(vinylidene fluoride) and poly(aminophenylboronic acid). Also disclosed is a method of fabricating a non-enzymatic glucose biosensor based on an electrospun nanofibrous membrane by depositing the composition on an electrode.

4 Claims, 2 Drawing Sheets

COMPOSITION FOR GLUCOSE SENSING COMPRISING OF NANOFIBROUS MEMBRANE AND METHOD FOR MANUFACTURING NON-ENZYMATIC GLUCOSE BIOSENSOR USING THE SAME

CROSS REFERENCE TO RELATED APPLICATIONS

This application is a 35 U.S.C. §371 National Phase Entry Application from PCT/KR2008/006309, filed Oct. 24, 2008, and designating the United States, which claims priority under 35 U.S.C. §119 to Korean Patent Application No. 10-2008-0074282 filed Jul. 29, 2008, which is incorporated herein in its entirety.

TECHNICAL FIELD

The present invention relates to a composition for glucose sensing obtained by dispersing in a organic solvent such as acetone a nanofibrous membrane fabricated by electrospinning a mixture containing a host polymer such as poly(vinylidene fluoride)polyacronitrile etc. and a functional polymer having amine and boronic acid groups such as and poly (aminophenylboronic acid), and to a method of fabricating a non-enzymatic glucose biosensor based on an electrospun nanofibrous membrane using the composition.

BACKGROUND ART

Diabetes mellitus is a metabolic disorder that results from insulin deficiency and is reflected by blood glucose concentrations being outside the normal range of 80-120 mg/dL (4.4-6.6 mM) [Ann. Intern. Med. 2007, 146, ITC1-15]. Diabetes causes complications such as neuropathy, nephropathy and retinopathy which result in heart disease, kidney failure, or blindness, respectively [Klonoff D C. Noninvasive blood glucose monitoring, Diabetes Care 1997; 20: 433-437]. Therefore, in order to treat diabetes, it is very important for diabetics to control their blood glucose levels by conducting self-monitoring several times a day. Indeed, glucose biosensors account for about 85% of the entire biosensor market. Such a huge demand in the market makes diabetes a model disease for developing new biosensing concepts.

A wide variety of methods for glucose analysis, including electrochemistry, near infrared spectroscopy, optical rotation and the like, have been reported in the literature [Yokowama, K., Sode, K., Tamiya, E., Karube, I. Anal. Chim. Acta (1989), 218, 137; Rabinovitch, B., March, W. F., Adams, R. L. Diabetes Care (1982), 5, 254; G. M., Moses, R. G., Gan, I. E. T., Blair, S. C. Diabetes Res. Clin. Pract. (1988), 4, 177; D_Auria, S., Dicesare, N., Gryczynski, Z., Gryczynski, I.; Rossi, M.; Lakowicz, J. R. Biochem. Biophys. Res. Commun. (2000), 274, 727]. The most commonly used technology for blood glucose determination is an enzyme-based method.

Electrochemical glucose monitoring has greatly contributed to improving the lives of diabetic patients. Despite the impressive progress in the development of electrochemical glucose biosensors, there are still many challenges and obstacles related to the achievement of a highly stable, enzyme-free and reliable glucose monitoring devices. The development in the last five decades is summarized in a recent review [J. Wang, Chem. Rev. 2008, 108, 814~825].

In general, the detection of glucose by electrochemical biosensors is based on the electrochemical oxidation of hydrogen peroxide generated by enzyme-catalyzed oxidation of glucose at anodic potentials (>+0.6 V vs. Ag/AgCl) [J. Wang, N. Naser, L. Anges, W. Hui, L. Chen, Anal. Chem. 64 (1992) 1285-1288]. However, at this relatively high potential, there may be interferences from other oxidizable species such as ascorbic acid, uric acid and acetaminophen. The glucose oxidase (GOx) based-glucose devices rely on the use of oxygen as the physiological electron acceptor, and they are subject to errors resulting from fluctuations in the oxygen pressure and the stoichiometric limitation of oxygen. Few strategies have been evolved to circumvent the oxygen deficiency [Wang, J.; Mo, J. W.; Li, S. F.; Porter, J. Anal. Chim. Acta (2001), 441, 183; D'Costa, E.; Higgins, I., Turner, A. P. Biosensors (1986), 2, 71]. Also, innovative methodologies have been adapted for establishing and tailoring the electrical contact between the redox center of GOx and electrode surfaces to improve the electron transport [Pishko, M. V., Katakis, I., Lindquist, S. E., Ye, L., Gregg, B. A., Heller, A. Angew. Chem., Int. Ed. (1990), 29, 82; Riklin, A., Katz, E., Willner, I., Stocker, A., Buckmann, A. F. Nature (1995), 376, 672].

Recently, research studies have been focused on eliminating the mediator and developing a reagentless glucose biosensor with a low operating potential close to the redox potential of the enzyme. In this case, the electron is transferred directly from glucose to the electrode via the active site of the enzyme. The absence of mediators is the main advantage of such third-generation biosensors and results in a very high selectivity (owing to the very low operating potential). The development in nanotechnology has inspired the application of nanomaterials in bioanalytical chemistry.

For the fabrication of a high-efficiency biosensor, the selection of a substrate matrix for dispersing the sensing material decides the sensor performance. It is highly desirable to use the substrates that high-surface area, optimum porosity, high thermal stability, chemical inertness and minimum or negligible swelling in aqueous and non-aqueous solutions. Electrospun fibrous membranes meet many of the requirements for achieving improved performance for a sensor electrode. The chief advantages of electrospun fibrous materials include design flexibility, dimensional stability upon the flow of gases and liquids through fiber bundles, high-surface area, safer operations, ease of scaling up, and reusability. Electrospun nanofibrous materials high surface area-to-volume ratios which are suitable for improving biosensor characteristics. Biological molecules can be immobilized onto the surface of electrospun membranes. However, the molecules on the surface of electrospun fibers tend to leach out when the fibrous mat is placed in a solution. It is therefore important to minimize the leaching of the biomolecules/enzymes within the fibrous mat using an additional functional material that can bind the biological molecules/enzymes.

Glucose was assayed amperometrically by the GOx-electroreduction of a ferricinium cation to a ferrocene, which was then electrooxidized on the screen printed carbon-paste electrode of a strip [Kyvik, K. O., Traulsen, J., Reinholdt, B., Froland, A. Diabetes Res. Clin. Pract. (1990), 10, 8590]. Home blood-glucose monitors utilize plastic or paper strips comprising electrochemical cells and contain PQQGDH, NAD-GDH, FAD-GDH or GOx and a redox mediator. These glucose monitors can utilize amperometry or chronoamperometry or coulometry.

The enzyme-based glucose sensors have a lot of problems in terms of the stability of the enzyme, oxygen dependence, the role of the mediator, enzyme leaching, etc. GOx quickly loses its activity below pH 2 and above pH 8, and is rapidly deteriorated at a temperature higher than 40° C. (R. Wilson, A. P. F. Turner, Biosens. Bioelectron. 7 (1992) 165]. Relatively high or low humidity may adversely affect the storage and use of the sensors. Due to these problems, the development of an enzymeless glucose sensor is required.

For the development of a practical non-enzymatic glucose sensor, suitable electrocatalysts have been used. Platinum surfaces modified by a heavy metal such as Tl, Pb, Bi, or $WO_3$ exhibited catalytic activity for glucose oxidation [G. Kokkinidis, N. Xonoglou, Bioelectrochem. Bioenerg. 14 (1985) 375; G. Wittstock, A. Strubing, R. Szargan, G. Werner, J. Electroanal. Chem. 444 (1998) 61; X. Zhang, K.-Y. Chan, J.-K. You, Z.-G. Lin, A. C. C. Tseung, J. Electroanal. Chem. 430 (1997) 147]. However, the catalytic oxidation has been limited to acidic or basic conditions. Non-enzymatic glucose sensors have been fabricated using nanoporous platinum [S. Park, T. D. Chung, H. C. Kim, Anal. Chem., (2003), 75, 3046; H. Boo, S. Park, B. Ku, Y. Kim, J. H. Park, H. C. Kim, T. D. Chung, J. Am. Chem. Soc., (2004), 126, 4524]. Most of the non-enzymatic glucose sensors, which have been suggested to date, have no glucose-recognition unit.

Recently, the present inventors have demonstrated the utilities of a non-enzymatic glucose sensor based on an electrospun nanoporous functional membrane [K. M. Manesh, P. Santhosh, A. Gopalan, Kwang-Pill Lee, Analytical Biochemistry, 2007, 360, 189]. A novel sensor electrode based on a composite electrospun nanofiberous membrane of poly(vinylidene fluoride) (PVdF) and poly(aminophenylboronic acid) (PAPBA) was fabricated on an indium tin oxide (ITO)-coated glass plate. The glucose-sensing ability of the nanofibrous membrane was assessed and, as a result, the PVdF/PAPBA-NFM exhibited an excellent linear response to the detection of glucose in the concentration range of 1 to 15 mM within a response time of less than 6 seconds. The PVdF/PAPBANFM fabricated through an electrospinning process enabled glucose to be detected with high selectivity and sensitivity even in the presence of other carbohydrates and showed negligible interference, reproducibility, and storage stability. The excellent performance of the nanofibrous membrane is attributable to its lager surface area and active sites suitable for glucose sensing. The electrospun membrane-based glucose sensor is ideal for glucose sensing in flowing streams. However, the process of fabricating the biosensor by depositing the electrospun PVdF/PAPBA-NFM directly on the electrode surface (ITO) has a problem in that it is difficult to control the thickness and uniformity of the surface.

DISCLOSURE

Technical Problem

Accordingly, it is required to develop a simple and efficient method for fabricating a non-enzymatic glucose sensor using an electrospun PVdF/PAPBA known as a glucose-sensing material having excellent sensitivity, selectivity and stability.

Technical Solution

To satisfy the above requirement, the present inventors have effectively improved a non-enzymatic glucose sensor-fabricating process by adopting a method of dispersing the electrospun PVdF/PAPBA-NFM in a solvent such as acetone and depositing the solution on an electrode, rather than a method of allowing a PVdF/PAPBA-NFM mixture to be deposited directly on an electrode surface during electrospinning of the PVdF/PAPBA-NFM mixture.

Hereinafter, the present invention will be described in detail.

In one aspect, the present invention relates to a composition for glucose sensing, which comprises a material obtained by dissolving in a solvent a nanofibrous membrane fabricated by electrospinning a mixture containing poly(vinylidene fluoride) and poly(aminophenylboronic acid). Herein, the solvent may additionally contain few more additive.

The inventive composition for glucose sensing is useful for fabricating non-enzymatic glucose biosensors and is characterized in that it is prepared using, as active materials for glucose sensing, electrospun poly(vinylidene fluoride) (PVdF) and poly(aminophenylboronic acid) (PAPBA), the sensitivity and selectivity of glucose sensing and stability of which were demonstrated in the previous study of the present inventors. Preferably, in the inventive composition, PVdF and PAPBA are contained at a ratio of 90-99 wt %:10-1 wt %.

Also, because the composition of the present invention is prepared using electrospun PVdF/PABA, it has the general characteristics (e.g., large surface area) of a nanofibrous membrane fabricated by electrospinning, and thus is advantageously applied as a biosensor.

The composition of the present invention is characterized in that it is obtained by dispersing in a suitable solvent a PVdF/PABA nanofibrous membrane fabricated by electrospinning. The solvent may be one or a mixture of two or more selected from the group consisting of hydrochloric acid, sulfuric acid, dimethylformamide, diethyl ether, acetone, chloroform, methanol, isopropyl alcohol, methyl ethyl ketone, tetrahydrofuran, toluene, benzene and xylene, but the scope of the present invention is not limited thereto. Preferably, the solvent is acetone.

The solvent which is used to disperse the electrospun nanofibrous membrane may contain, as additives, a variety of film-forming polymers known in the art for various purposes of, for example, improving the heat resistance and chemical resistance of the nanofibrous membrane in the composition or improving the performance in the fabrication process of biosensors.

In another aspect, the present invention relates to a method for fabricating a non-enzymatic glucose biosensor based on a nanofibrous membrane, the method comprising the steps of: (i) electrospinning a mixture containing poly(vinylidene fluoride) and poly(aminophenylboronic acid) to fabricate an electrospun nanofibrous membrane; (ii) dispersing in a solvent the electrospun nanofibrous membrane obtained in step (i) to prepare a composition for glucose sensing; and (iii) depositing on an electrode the glucose sensing composition obtained in step (ii). Herein, the solvent in step (i) may additionally contain an additive.

Steps (i) and (ii) are carried out to prepare the inventive composition for glucose sensing which can be used immediately to fabricate a glucose biosensor after being dispersed in a suitable solvent.

Specifically, step (1) can be carried out according to any conventional process of fabricating an electrospun PVdF/PABA nanofibrous membrane or spinning a low-viscosity polymer into a fiber form. In a process of dissolving a polymer in a solvent to prepare a viscous spinning solution and in a process of electrospinning the spinning solution at a predetermined voltage and spinning distance, the solvent kind and concentration and the spinning distance, voltage and method can be selected and varied in a wide range depending on the intended use of the composition. The solvent which can be used in the step (ii) is as described above.

The composition for glucose sensing obtained in steps (i) and (ii) can be deposited on an electrode according to any method known in the art. Specifically, examples of the method of depositing the composition include spin coating, dip coating, roll coating, screen coating, spray coating, spin casting, flow coating, screen printing, inkjet coating and drop casting.

An electrode which can be used to fabricate the biosensor of the present invention may be any conventional or screen-printed electrode for current measurement. Examples of the electrode include, but are not limited to, an ITO electrode and a ZnO/ITO electrode.

FIG. 1 schematically shows a process for fabricating the inventive non-enzymatic glucose biosensor based on the electrospun nanofibrous membrane.

Advantageous Effects

The inventive composition prepared by dispersing electrospun PVdF/PAPBA in a solvent maintains excellent sensitivity, selectivity and stability for glucose sensing, and thus can be effectively used to fabricate a biosensor.

According to the present invention, the prior inconvenient and complicated process of depositing PVdF/PAPBA-FM directly on an electrode during electrospinning of PVdF/PAPBA-FM is improved, and a method of fabricating a biosensor in a simple and efficient manner is provided. In addition, the fabrication method of the present invention is advantageous in that it enables a sophisticated biosensor for glucose sensing to be fabricated, has high process reproducibility and is commercially easily applied.

BEST MODE

Figure 1:
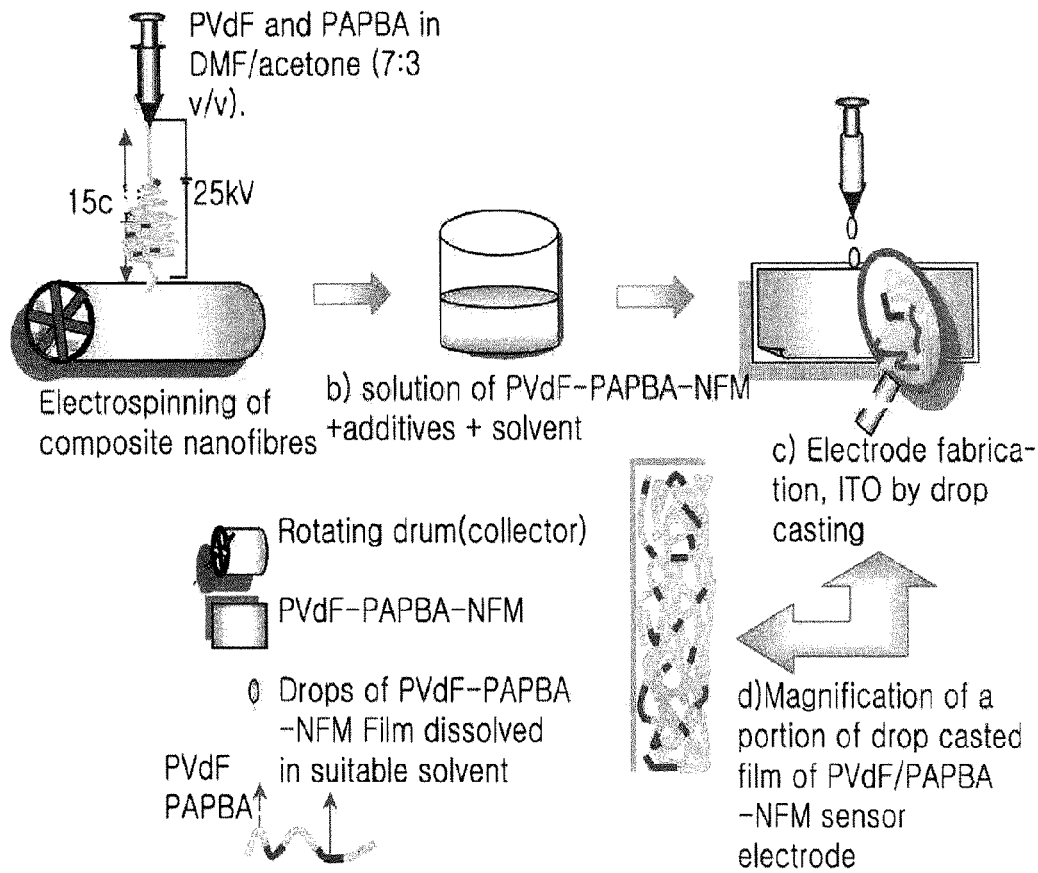
FIG. 1 shows a process for fabricating a glucose sensor electrode based on a PVdF/PAPBA-NFM film.

Hereinafter, the present invention will be described in further detail with reference to examples. It is to be understood, however, that these examples are for illustrative purposes and are not to be construed to limit the scope of the present invention.

Example 1

Chemicals

3-Aminophenylboronic acid, PVdF and glucose were of analytical grade and used as received. An aqueous solution of glucose was prepared afresh at the time of performing amperometric experiments in phosphate buffer (pH 7). Before performing the experiment, the surface of an ITO-coated plate was degreased with acetone and rinsed further with distilled water. Double distilled water was used throughout the experiment.

MODE FOR INVENTION

Example 2

Preparation of Electrospun PVdF-PAPBA Composite Membrane 2-1: Preparation of PAPBA Poly(3-aminophenylboronic acid) (PAPBA) was prepared by oxidative polymerization of 3-aminophenylboronic acid (50 mM in 1M HCl) using ammonium persulfate as an oxidant at 5° C. The blackish green-colored precipitate, PAPBA, was filtered, washed with water, and dried.

2-2: Preparation of Electrospun PVdF-PAPBA Fibrous Membrane

Adequate amounts of PVdF (8 g) and PAPBA (0.25 g) were dissolved in an N,N-dimethylformamide/acetone mixture to obtain a composite solution. Electrospinning of the composite solution was performed at a flow rate of 1 mL/h with a potential difference of 25 kV. An aluminium foil was wrapped on the surface of a collector drum. The composite membrane was collected on the aluminum foil.

2-3: Preparation of Electrospun PVdF-PAPBA Sensor Electrode

The electrospun PVdF-PAPBA membrane was dissolved in acetone and drop-coated on the surface of a suitable electrode (ITO or glassy carbon, etc) with polymer Nafion solution.

2-4: Amperometric Studies for Glucose Detection

Electrochemical experiments were carried out using an Iviumstat Electrochemical interface (Netherlands). For the electrochemical experiments, a standard single-compartment electrochemical cell containing the electrospun PVdF-PAPBA as a working electrode, and Ag/AgCl and platinum serving as reference and auxiliary electrodes, respectively, was employed.

Amperometric studies were performed at electrospun PVdF-PAPBA-modified electrodes for various concentrations of glucose. The potential was set at 0.30 V, and the current-time curves were recorded after the successive additions of 50 μL of glucose (0.1M PBS, pH=7.0). The background current response of the sensor electrode was allowed to reach a steady state. When the background current was stable, a solution of glucose was injected into the electrolytic cell, and its response was measured.

Example 3

PVdF/PAPBA and Fabrication of Glucose Sensor

Three essential requirements for a material having good sensor characteristics are sensitivity, selectivity and mechanical stability. Components chosen for the fabrication of an electrochemical sensor electrode should satisfy these three requirements. Furthermore, the sensor electrode fabrication processes should be reproducible and able to be applied for commercial purposes in a simple manner.

In the present invention, an electrospun PVdF/PAPBA fibrous membrane (PVdF/PAPBA-FM) electrode for glucose was fabricated. It is important to note that the sensor electrode was fabricated without any enzyme or additional mediator. Ultimately, the scientists are aiming to eliminate the mediator and develop a reagent-less glucose biosensor having a low operating potential close to the redox potential of the enzyme. In this case, an electron is transferred directly from glucose to the electrode via the active site of the enzyme. The absence of any mediator is the main advantage of such third-generation biosensors, leading to a very high selectivity (owing to the lower operating potential).

It must be noted that commercialization of non-enzymatic glucose sensors working in human blood is a challenging task. Future research on non-enzymatic glucose sensors requires disposable strips based on third generation non-enzymatic glucose sensors for determining human blood glucose levels. Besides, the sensor materials must be loaded into the device by a simple procedure so as to combine with sophisticatedly engineered microfluidic chips. Ultimately, a portable glucometer for multiple uses is to be fabricated with the sensor material.

Herein, a simple methodology compared to a complicated procedure that is required for the fabrication of metal or alloy based non-enzymatic glucose sensors was adapted for the fabrication of a non-enzymatic glucose sensor [C. D. Garcia, C. S. Henry, Anal. Chem., (2003), 75, 4778; J.-S. Ye, Y. Wen, W. D. Zhang, L. M. Gan, G. Q. Xu, F.-S. Shen, Electrochem. Commun., (2004), 6, 66; H. Boo, S. Park, B. Ku, Y. Kim, J. H. Park, H. C. Kim, T. D. Chung, J. Am. Chem. Soc. (2004), 126, 4524; Y. Sun, H. Buck, T. E. Mallouk, Anal. Chem., (2001), 73, 1599]. Nanoporous metal electrodes were fabricated by de-alloying in acidified conditions, and the sensor material was prepared. In the previous report, the present inventors achieved good sensitivity, selectivity and stability towards glucose detection for the electrospun PVdF/PAPBA-FM electrode. However, the electrode fabrication process of depositing PVdF/PAPBA-FMs directly on the electrode while performing electrospinning was cumbersome and tricky.

In the present invention, the sensor material, electrospun PVdF/PAPBA, that was tested for sensitivity, selectivity and stability of glucose detection, was used, and the electrospun PVdF/PAPBA-FM was dissolved in suitable solvent and mixed with additives. The solution of PVdF/PAPBA-FM is suitable to cast onto the surface of any conventional or screen-printed electrode.

In the present invention, the use of a variety of aqueous solvents, such as hydrochloric acid or sulfuric acid, and non-aqueous solvents, such as DMF, diethyl ether, acetone, chloroform, methanol, tetrahydrofuran, toluene, benzene, xylene, etc., was attempted. Among these solvents, acetone that is most effective in preparing solution processable electrospun nonwoven fibers of PVdF-PAPBA was selected. The dispersed fibers were then cast on the surface of ITO to form a thin film. FIG. 1 shows the process for fabricating the PVdF/PAPBA-FM film glucose sensor electrode. The fabricated electrode was stable.

In the prior art, a non-enzymatic glucose sensor based on potentiometry using polymer coatings was developed [E. Shoji, M. S. Freund, J. Am. Chem. Soc., (2001), 123, 3383.; E. Shoji, M. S. Freund, J. Am. Chem. Soc., (2002), 124, 12486.] The electrochemical potential that was developed across the polymer membrane was sensitive to the pKa of the conducting polymer as a result of boronic acid-diol complexation. This system actually worked as expected and offered a new opportunity for a potentiometric glucose sensor free of an enzyme. However, the lack in selectivity for glucose limited the practical use of the developed non-enzymatic glucose sensor. Usually, fluoride ions are added along with aminophenylboronic acid to convert the $sp^3$-hybridized boronate group of aminophenylboronic acid to an $sp^2$-hybridized boronate group in order to achieve the hydroxylation of glucose molecules. However, such a procedure is not suitable for the fabrication of an electrode which is stable in aqueous buffer conditions that are needed for glucose or serum analysis.

Under dynamic conditions in glucose sensing, there is a possibility of removal of $F^-$ ions from the PAPBA film. As a consequence of leaching of $F^-$ ions from the sensor matrix, the sensitivity of the glucose sensor may be significantly lowered upon long-term use. The fluoride ions will be leached out from the sensor environment during analysis in an aqueous system.

The PVdF/PAPBA-FM film sensor has a stable environment and free from the problems associated with leaching of fluoride ions. In the PVdF/PAPBA-FM film, the chains of PAPBA are interlinked with the mechanically stable matrix of PVdF. The electrospinning conditions are favorable for such molecular interactions. Sensitivity towards glucose arises from the interactions of C-F groups of PVdF with amine or imine units of PAPBA. In the present invention, PVdF has C-F groups, and the interconnected morphology in the composite gives close proximity for the fluorine atoms to access the boron atoms which eventually may favor complexation with glucose. Hence, the problem associated with leaching of the fluorine source from the sensor matrix is negligible in the present invention.

Figure 2:
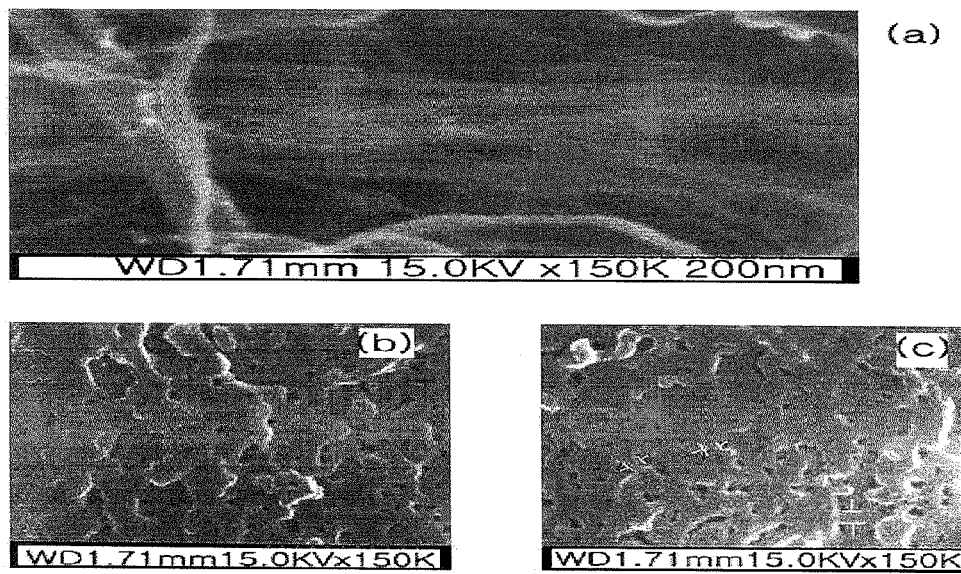
FIG. 2(a) is an FESEM image of an electrospun PVdF/PAPBA film deposited directly on the surface of ITO, and FIGS. (b) and (c) are FESEM images of an electrospun PVdF/PAPBA film recorded in different regions.

FIG. 2a shows an FESEM image of electrospun PVdF/PAPBA fibers deposited directly on the surface of ITO, and an electrospun PVdF/PAPBA film is fabricated by dispersing the electrospun PVdF/PAPBA fibers in a suitable solvent and casting the solution. Importantly, the electrospun PVdF/PAPBA film has interconnected fibers with a polymer layer (FIG. 2b). The electrospun PVdF/PAPBA fibers have the interconnected morphology (FIG. 2a). The fibers are twisted and interlocked to each other. The fibers are flattened in shape and have a decreased diameter (around 100 nm) compared to the diameter of pristine PVdF (around 300 nm). A comparison of the FESEM image of the electrospun PVdF/PAPBA fibers deposited directly on the surface of ITO with the electrospun PVdF/PAPBA film obtained by dispersing the electrospun PVdF/PAPBA fibers in a suitable solvent and casting the solution clearly indicates that the fibrous morphology of the electrospun PVdF/PAPBA film is maintained. However, the electrospun PVdF fibers are rigid and straight with negligible twisting between the fibers. The diameter of the fibrous structure observed on the drop cast material was found to be about 100 nm.

The nanofibrous morphology of the electrospun PVdF/PAPBA film provides a large surface area and glucose sensing characteristics glucose. The interconnected network morphology of the electrospun PVdF/PAPBA composite is attributable to the intermolecular interactions between the $NH_2$ groups in PAPBA and the C-F group in PVdF. The molecular interactions between PVdF and PAPBA are evident from the shifts in the positions of $CF_2$ stretching and $CF_2$ wagging bands with respect to the bands in simple PVdF. The presence of a band corresponding to quinoid imine stretching (1600 $cm^{-1}$) in the FT-IR spectrum of PVdF/PAPBA-NFM indicates that PAPBA exists in a self-doped state.

Figure 3:
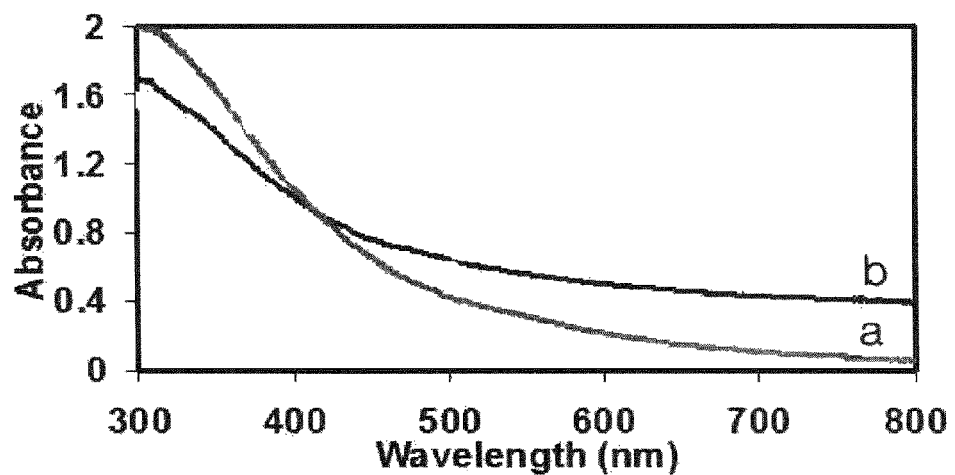
FIG. 3(a) shows UV-visible spectra of an electrospun PVdF-PAPBA film (a) and pristine PAPBA (b).

The presence of PABA in the electrospun PVdF/PAPBA film was verified by UV-visible spectroscopy. The UV-visible spectrum of the electrospun PVdF-PAPBA film is shown in the FIG. 3. The UV-visible spectrum of PVdF-PAPBA-film shows two optical bands around 310 nm and 530 nm. These bands are attributed to the pi-pi* transition and polaronic band of PAPBA. This is further confirmed from the UV-Visible spectrum of pristine PABA and PVdF. It is to be noted that the pristine PVdF does not exhibit any peak in the UV-visible region. The UV-visible spectrum of PAPBA shows bands around 310 nm and 530 nm. Similar spectral features are found in the electrospun PVdF/PAPBA film and pristine PAPBA.

Amperometry is an electrochemical technique for determining a response current proportional to an analyte in a solution. The amperometric technique is an important technique in determining the concentration of a solution. Also it is fast, simple and reliable technique.

Figure 4:
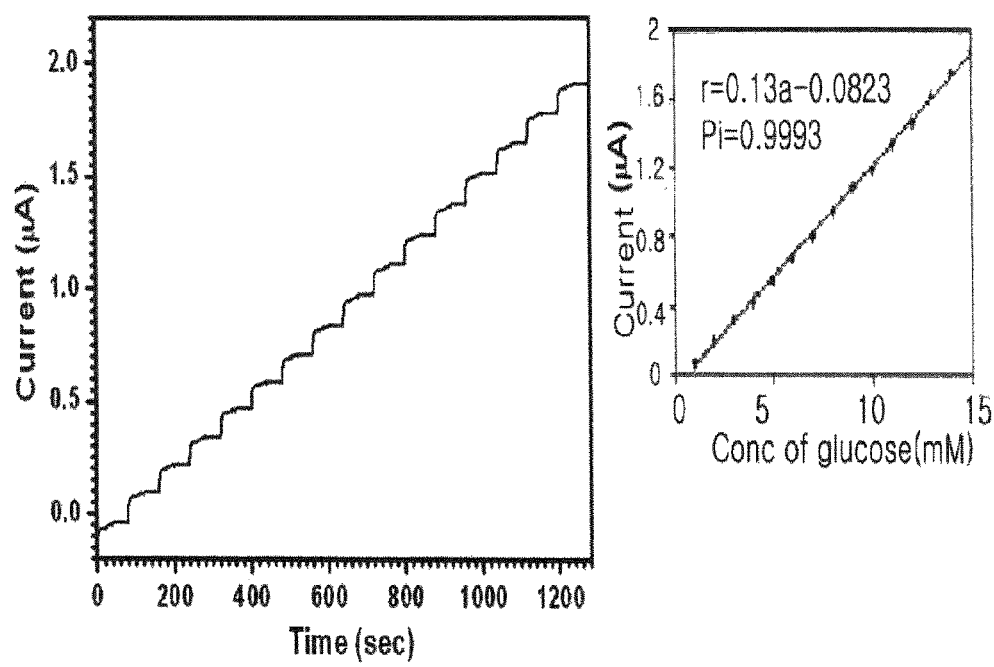
FIG. 4 shows the amperometric response of a PVdF/PABA-FM to glucose, and an inset in FIG. 4 is a concentration-current plot of an electrode.

FIG. 4 shows a current-time curve obtained by PVdF/PAPBA-FM for the successive addition of 1 mM glucose in phosphate buffer (pH=7) for an operating potential of 0.30 V. When the background current became stable, glucose was added into the electrolyte (phosphate buffer). The current response for the successive addition of glucose was measured. An increasing amperometric response was observed for successive addition of glucose (FIG. 4). The current at the PVdF/PAPBA-FM electrode increased successively and reached a stable value for successive addition of a glucose concentration up to 15 mM. The response time was only 6 seconds, which was lower than that of other reported glucose sensors. An inset in FIG. 4. shows a calibration plot of glucose concentration vs. current. The current response was found to be linear in the glucose concentration range of 1-15 mM with a sensitivity of 1.84 mAmM$^{-1}$. Thus, the fibrous membrane shows a high sensitivity to glucose in comparison with other glucose sensors.

INDUSTRIAL APPLICABILITY

As described above, the present invention provides an effective method for fabricating a non-enzymatic glucose biosensor based on an electrospun nanofibrous membrane. The non-enzymatic glucose biosensor according to the present invention can be widely used in the medical field for clinical diagnosis.

The invention claimed is:

1. A non-enzymatic glucose sensor comprising an electrode on which a polymer solution is deposited, wherein said polymer solution is, obtained by dispersing in a solvent a nanofibrous membrane fabricated by electrospinning a mixture comprising poly(vinylidene fluoride) and poly(aminophenylboronic acid).

2. The non-enzymatic glucose sensor of claim 1, wherein the poly(vinylidene fluoride) and the poly(aminophenylboronic acid) are present at a ratio of 90-99 wt %:10-1 wt % based on the total weight of poly(vinylidene fluoride) and the poly(aminophenylboronic acid).

3. The non-enzymatic glucose sensor of claim 1, wherein the solvent additionally comprises an additive.

4. The non-enzymatic glucose sensor of claim 1, wherein the solvent is one or more selected from the group consisting of hydrochloric acid, sulfuric acid, dimethylformamide, diethyl ether, acetone, chloroform, methanol, isopropyl alcohol, methyl ethyl ketone, tetrahydrofuran, toluene, benzene and xylene.

* * * * *